United States Patent
Lu et al.

(10) Patent No.: US 10,222,345 B2
(45) Date of Patent: Mar. 5, 2019

(54) ACETIC ACID GAS SENSOR BASED ON AZOBENZENE COMPOUND, PREPARATION METHOD AND APPLICATION THEREOF

(71) Applicant: Soochow University, Suzhou, Jiangsu (CN)

(72) Inventors: Jianmei Lu, Jiangsu (CN); Jinghui He, Jiangsu (CN)

(73) Assignee: SOOCHOW UNIVERSITY, Suzhou (CN)

( * ) Notice: Subject to any disclaimer, the term of this patent is extended or adjusted under 35 U.S.C. 154(b) by 220 days.

(21) Appl. No.: 15/405,358

(22) Filed: Jan. 13, 2017

(65) Prior Publication Data

US 2017/0205367 A1 Jul. 20, 2017

(30) Foreign Application Priority Data

Jan. 14, 2016 (CN) .......................... 2016 1 0024206

(51) Int. Cl.
*G01N 27/12* (2006.01)
*G01N 33/00* (2006.01)
*C23C 14/02* (2006.01)
*C23C 14/24* (2006.01)
*C23C 14/12* (2006.01)

(52) U.S. Cl.
CPC ......... *G01N 27/125* (2013.01); *C23C 14/021* (2013.01); *C23C 14/12* (2013.01); *C23C 14/24* (2013.01); *G01N 33/0047* (2013.01)

(58) Field of Classification Search
CPC ............................... G01N 27/12; G01N 33/00
USPC .............. 422/82.01–82.03, 98; 436/129, 149
See application file for complete search history.

(56) References Cited

U.S. PATENT DOCUMENTS

| 3,743,589 | A * | 7/1973 | Nicholas | G01N 27/30 204/406 |
| 6,921,668 | B2 * | 7/2005 | Travers | C12Q 1/04 436/113 |
| 9,841,411 | B2 * | 12/2017 | Lu | G01N 33/0054 |

(Continued)

FOREIGN PATENT DOCUMENTS

JP       1-223339       * 9/1989

OTHER PUBLICATIONS

Kim, Y. J. et al, IEEE Sensors 2005, 845-848.*

(Continued)

*Primary Examiner* — Arlen Soderquist
(74) *Attorney, Agent, or Firm* — SZDC Law P.C.

(57) ABSTRACT

An acetic acid gas sensor based on an azobenzene compound includes an interdigital electrode and a coating material. The coating material is an azobenzene compound of formula I. The coating material is plated on the interdigital electrode through a vacuum coating process, and a thickness of the coating material is 100-200 nm.

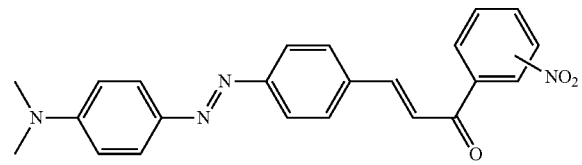

7 Claims, 3 Drawing Sheets

(56) References Cited

U.S. PATENT DOCUMENTS

| | | | | |
|---|---|---|---|---|
| 2003/0044996 A1* | 3/2003 | Travers | ............... | G01N 33/487 436/129 |
| 2004/0127808 A1* | 7/2004 | Vaughan | ............... | A61B 5/083 600/532 |
| 2004/0194535 A1* | 10/2004 | Su | ...................... | G01N 27/128 73/31.06 |
| 2010/0203623 A1* | 8/2010 | Zhou | ................... | B01J 20/3057 435/287.9 |

OTHER PUBLICATIONS

Simon, F.-X. et al, New Journal of Chemistry 2009, 33, 2028-2033.*
Panigrahi, S. et al, Materials Science and Engineering C 2012, 32, 1307-1313.*
Gomez-Rivera, Bioorganic & Medicinal Chemistry Letters 2013, 23, 5519-5522.*
Rohini, R. M. et al, Der Pharma Chemica 2015, 7, 77-83.*
Ndiaye, A. L. et al, Journal of Sensors 2015, Article 290598, 7 pages.*

* cited by examiner

ACETIC ACID GAS SENSOR BASED ON AZOBENZENE COMPOUND, PREPARATION METHOD AND APPLICATION THEREOF

This application claims priority to Chinese Patent Application No.: 201610024206.7, filed Jan. 14, 2017, which is incorporated by reference for all purposes as if fully set forth herein.

TECHNICAL FIELD

The invention belongs to the technical field of organic semiconductor material, in particular to acetic acid gas sensor based on azobenzene compound, its preparation method and its use in air quality detection, especially in acetic acid gas detection.

BACKGROUND ART

With the development of defense, environmental monitoring and protection nowadays, the demand for gas sensors has increased dramatically. Whether in refueling stations, food plants, gas stations commonly used in daily life, or in the experimental environment of scientific research, it is all in urgent need of a sensor with better performance and higher sensitivity than the existing sensors.

The traditional inorganic metal oxide sensor not only has high demand for the temperature of the working environment, but also responds to almost all organic gases, so that it has the shortcomings of bad practicality and poor selectivity.

The application range of electrochemical gas sensor is limited to the gas which can catalyze electrochemical reaction with the noble metal electrode, and its detection type is few, and there is baseline drift, easy poisoning and so on.

In contrast, the organic small molecule membrane gas sensor has the advantages of low operating temperature, high selectivity, easy to design and control of thin film devices, etc., gradually favored by the researchers.

INVENTION CONTENT

According to such situation, in the present invention, a gas sensor is prepared using one of three types of azobenzene-based conjugated small molecules (AZOC-2N, AZOC-3N, and AZOC-4N, respectively, as shown below), and observed at different gas concentrations the I-V curve of the sensor to detect different concentrations of acetic acid vapor. In order to detect the selectivity of the sensor, the present invention also detects hydroxyl-rich water and ethanol vapors at the same temperature, which proves that the sensor of the present invention has the advantages of low operating temperature and high selectivity.

AZOC-2N

AZOC-3N

AZOC-4N

More specifically, the present invention adopts the following technical scheme:

The application of an azobenzene compound of the formula I in the preparation of an acetic acid gas sensor,

I

The acetic acid gas sensor based on an azobenzene compound comprises an interdigital electrode and a coating material, said coating material is an azobenzene compound of the formula I shown as above, said coating material is plated on said interdigital electrode through the vacuum coating process, and the thickness of said coating material is 100-200 nm.

It is preferred that in the acetic acid gas sensor based on an azobenzene compound, said interdigitated electrode takes a layered structure of silicon, silicon dioxide (with the thickness of 270-330 nm, preferably 300 nm) and chromium (with the thickness of 9-11 nm, preferably 10 nm) in bottom-up sequence as a base, with the gold electrode (with the thickness of 90-110 nm, preferably 100 nm) arranged on said base; the interdigital width of said interdigital electrode is 3-8 um (preferably 5 um), the spacing of the interdigitals is 2-5 um (preferably 3 um).

The acetic acid gas sensor based on an azobenzene compound mentioned above is prepared through the preparation method comprising the steps as follows:

1) cleaning a substrate, and fixing the interdigital electrode on the substrate;

2) placing the substrate having the interdigital electrode fixed in step 1) into a vacuum coating apparatus, and charging the azobenzene compound of the formula I according to claim 1 into the vacuum coating apparatus as a coating material;

3) setting the vaccum deposition parameters as following: the deposition speed is 0.5-0.6 Å/s, the deposition pressure is 1 E-6-1 E-5 mbar, the deposition temperature is 120-140° C.;

4) after the parameter setting is completed, turning on the pressure reducing device to reduce the pressure inside the chamber of the vacuum deposition apparatus, when the chamber pressure is less than 5.0 mbar, turning on the molecular pump, when the pressure reaches the deposition pressure, beginning to evaporate the film until the desired thickness is reached, to get the acetic acid gas sensor based on an azobenzene compound.

Preferably, in the preparation method, the fixing in step 1) is accomplished by means of double-sided adhesive bonding.

Preferably, in the preparation method, the vacuum coating apparatus in step 2) is a vacuum coating machine.

Preferably, in the preparation method, the vaccum deposition parameters in step 3) is set as follows: the deposition speed is 0.5 Å/s, the deposition pressure is 1 E-5 mbar, the deposition temperature is 120° C.

Preferably, in the preparation method, the pressure reducing device in step 4) is a vacuum pump.

The application of said acetic acid gas sensor based on an azobenzene compound in air quality checking, especially in the detection of acetic acid gas.

Comparing with the prior art, this invention has the following advantages:

(1) The device is easy to prepare, and the operation is simple;

(2) Selectivity is high, the intensity of the sensor for acetic acid is much higher than other molecules containing hydroxyl;

(3) The test can be completed at room temperature, the dependence on ambient temperature is low.

DETAILED DESCRIPTIONS

Figure 1:
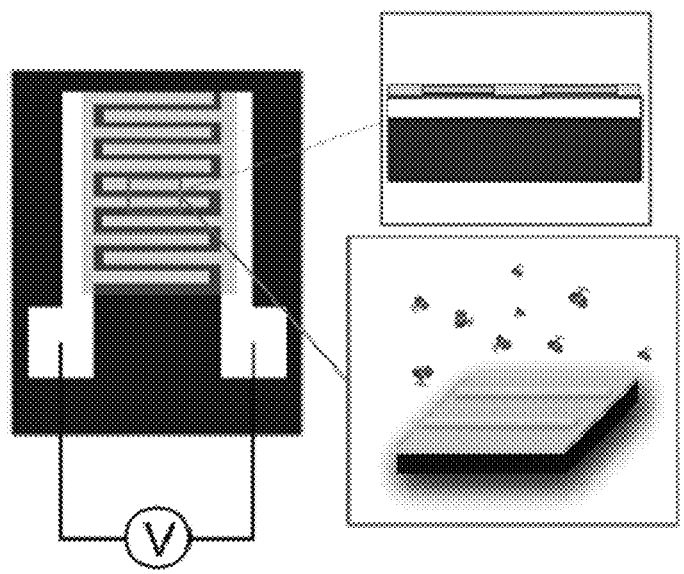
FIG. 1 is a schematic view of a gas sensor based on an azobenzene-based compound film.

The technical solution of the present invention will be further described hereinafter with reference to the accompanying drawings and specific examples. Unless otherwise indicated, reagents, materials, instruments, etc., used in the examples below may be obtained commercially.

Example 1: The Preparation of the Gas Sensor Based on an Azobenzene Organic Thin Film (1) Clean the glass substrate and bond the interdigital electrode on the substrate with a double-sided adhesive. The interdigitated electrode takes a layered structure of silicon, silicon dioxide (300 nm) and chromium (10 nm) in bottom-up sequence as a base, with the gold electrode (100 nm) arranged on; the interdigital width is 5 um, the spacing of the interdigitals is 3 um;

(2) Place the substrate having the interdigital electrode fixed in step 1) into a vacuum coating machine, weigh 35 mg of each of the three azobenzene compounds (AZOC-2N, AZOC-3N, AZOC-4N) separately and place in quartz crucibles, put the crucibles into the vacuum coating machine for use later;

(3) Set the vaccum deposition parameters as following: the deposition speed is 0.5 Å/s, the deposition pressure is 1 E-5 mbar, the deposition temperature is 120° C.;

(4) After the parameter setting is completed, turn on the vacuum pump to reduce the pressure inside the chamber of the vacuum coating machine, when the chamber pressure is less than 5.0 mbar, turning on the molecular pump (If the molecular pump were turned on when the pressure is too high, the molecular pump would be damaged so that the deposition pressure is hard to reach, and the quality of the film will be poor), when the pressure reaches 1 E-5 mbar, beginning to evaporate the film until the thickness reaches 100 nm, to get the acetic acid gas sensor based on an azobenzene compound. The structure of the sensor is shown in FIG. 1.

As can be seen from FIG. 1, the device is divided into five layers, from bottom to top re silicon, silicon dioxide, chromium, gold electrodes and azobenzene film.

Example 2: Testing the I-V Curve of Three Kinds of Organic Thin Film Sensors Under Different Concentration of Acetic Acid Open the N2 gas bottle, flow the pure N2 to the test device, to maintain the flow rate of 3 L/min, after 5 min, set the voltage to 0-40 V, measuring the interdigital electrode I-V curve background baseline.

The N2 flow rate is adjusted by a dynamic gas distribution device, obtain acetic acid gas with different concentration (6.8 to 27.0 ppm) by diluting saturated vapor of acetic acid at 15° C., measure the I-V curves of three gas sensors based on organic thin films (AZOC-2N, AZOC-3N, AZOC-4N) at different acetic acid vapor concentrations. The results are shown in FIGS. 2 to 4.

Figure 2:
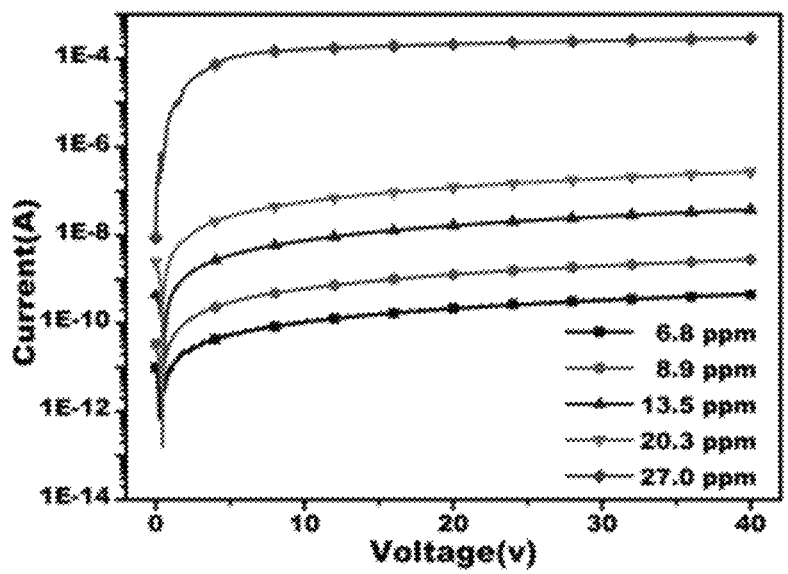
FIG. 2 shows the I-V curve of the gas sensor based on the AZOC-2N film for acetic acid vapor with a concentration of 6.8 to 27.0 ppm.
Figure 3:
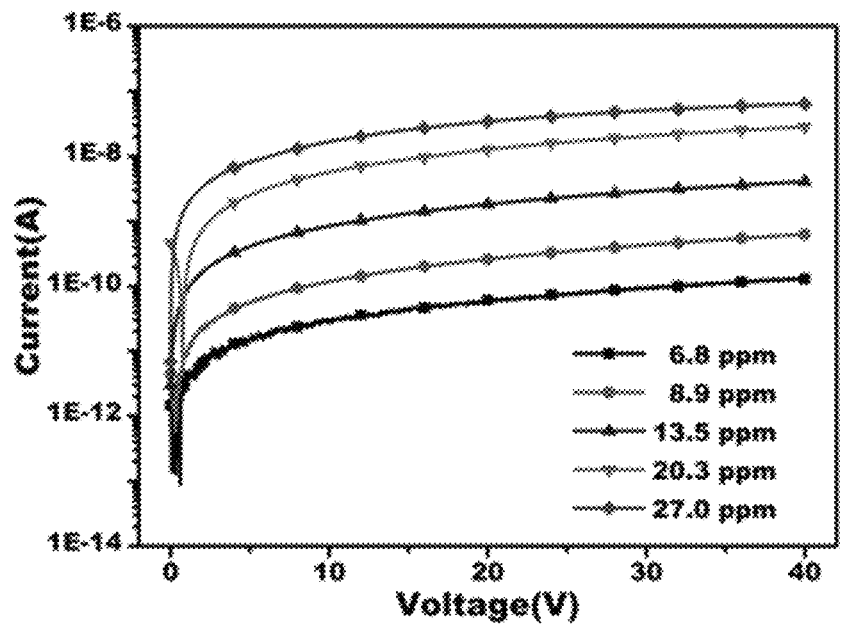
FIG. 3 shows the I-V curve of the gas sensor based on the AZOC-3N film for acetic acid vapor with a concentration of 6.8 to 27.0 ppm.
Figure 4:
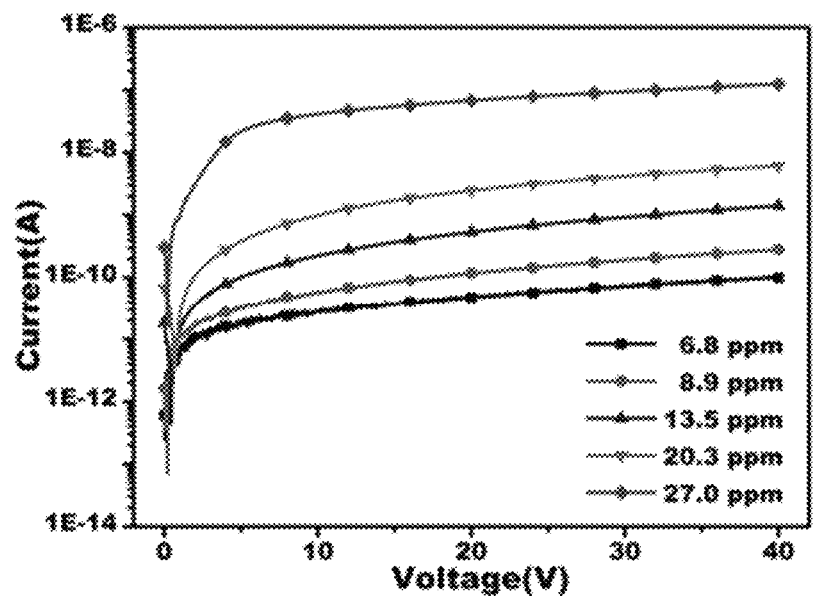
FIG. 4 shows the I-V curve of the gas sensor based on the AZOC-4N film for acetic acid vapor with a concentration of 6.8 to 27.0 ppm.

As can be seen from FIG. 2 to FIG. 4, the current response of the gas sensor increases with the increasing of gas concentration of acetic acid vapor.

Example 3: The Recoverability of the Gas Sensor Based on AZOC-2N Film for Different Concentrations of Acetic Acid Vapor By adjusting the inlet switch, alternately provide the acetic acid vapor and nitrogen into the test chamber, to test recoverability of the gas sensor based on AZOC-2N film, the results shown in FIG. 5.

Figure 5:
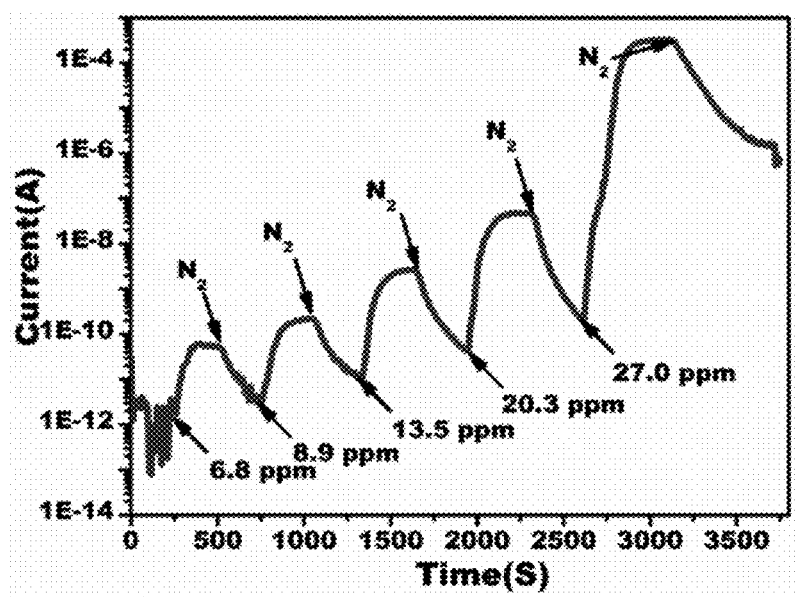
FIG. 5 shows the recoverability results of the gas sensor based on the AZOC-2N film.

As can be seen from FIG. 5, while the concentration of acetic acid vapor is increasing, the current will increase; meanwhile, when nitrogen is provided, the current value began to decline. It can be proved that the gas sensor based on AZOC-2N film is recoverable, and it is suitable for long-term and stable detection of acetic acid gas in the air.

Example 4: Selectivity Testing of Three Organic Thin Film Sensors

Figure 6:
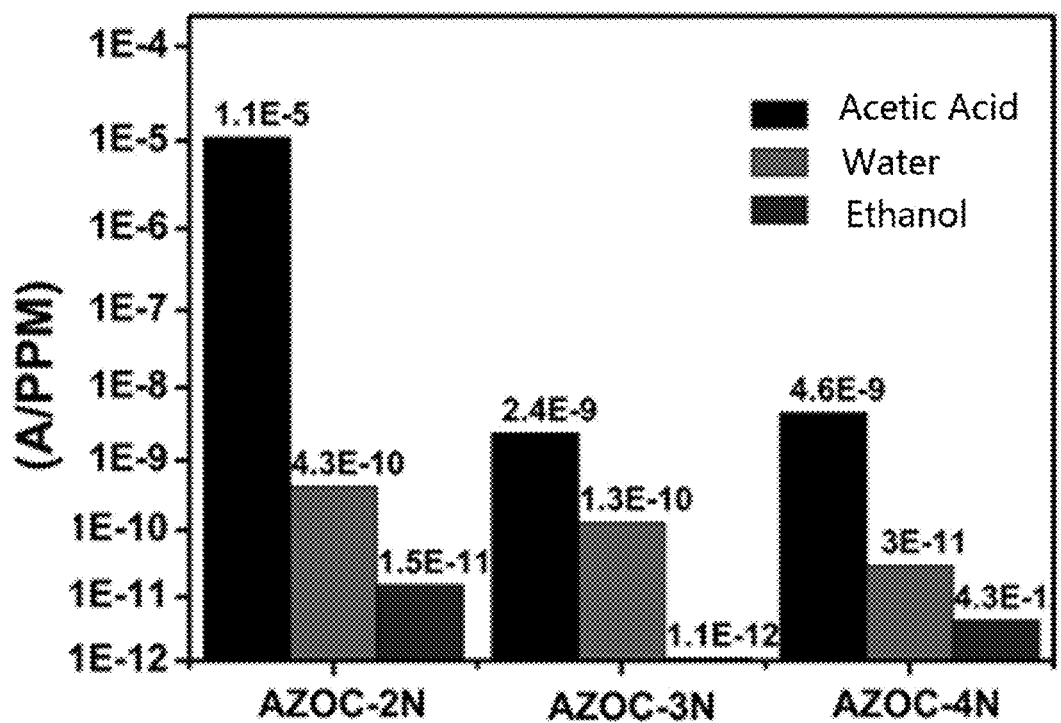
FIG. 6 shows the results of a selective experiment of the gas sensor based on an azobenzene-based compound film.

In order to detect the selectivity of the gas sensor, the hydroxyl-rich water and the ethanol vapor were detected at the same temperature, and the results are shown in FIG. 6.

As can be seen in FIG. 6, the change in current for acetic acid per ppm of the three film materials is much greater than that of water and ethanol, shows good selectivity, and AZOC-2N is the most responsive to acetic acid.

In summary, the preparation of a gas sensor based on AZOC-2N, AZOC-3N and AZOC-4N, which are organic azobenzene-based organic thin films, enables the detection of acetic acid molecules, which can be detected at room temperature and has high selectivity, compared with the existing sensor, has great application potential.

The invention claimed is:

1. An acetic acid gas sensor based on an azobenzene compound, comprising an interdigital electrode and a coating material, wherein said coating material is an azobenzene compound of formula I:

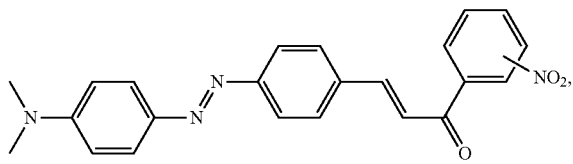

I and said coating material is plated on said interdigital electrode through a vacuum coating process, and said coating material is 100-200 nm thick.

2. The acetic acid gas sensor based on an azobenzene compound according to claim 1, wherein said interdigital electrode takes a layered structure of silicon, silicon dioxide and chromium in bottom-up sequence as a base, with a gold electrode arranged on said base;

said silicon dioxide is 270-330 nm thick, said chromium is 9-11 nm thick, and said gold electrode is 90-110 nm thick.

3. The acetic acid gas sensor based on an azobenzene compound according to claim 1, wherein the interdigital electrode has a width of 3-8 um and a spacing of 2-5 um.

4. A preparation method of the acetic acid gas sensor based on an azobenzene compound according to claim 1, which comprising the steps as follows:

1) cleaning a substrate, and fixing the interdigital electrode on the substrate;

2) placing the substrate having the interdigital electrode fixed in step 1) into a vacuum coating apparatus, and charging the azobenzene compound of the formula I into vacuum coating apparatus as a coating material;

3) setting the vaccum deposition parameters as following: a deposition speed is 0.5-0.6 Å/s, a deposition pressure is 1 E-6-1 E-5 mbar, a deposition temperature is 120-140° C.;

4) after the parameter setting is completed, turning on a pressure reducing device to reduce the pressure inside the chamber of the vacuum coating apparatus, when the chamber pressure is less than 5.0 mbar, turning on a molecular pump, when the pressure reaches the deposition pressure, beginning to evaporate the film until the desired thickness is reached, to get the acetic acid gas sensor based on an azobenzene compound.

5. The preparation method according to claim 4, wherein the fixing in step 1) is accomplished by means of double-sided adhesive bonding.

6. The preparation method according to claim 4, wherein the vaccum deposition parameters in step 3) is set as follows: the deposition speed is 0.5 Å/s, the deposition pressure is 1 E-5 mbar, the deposition temperature is 120° C.

7. The preparation method according to claim 4, wherein the pressure reducing device in step 4) is a vacuum pump.

* * * * *